(12) United States Patent
Glassman et al.

(10) Patent No.: US 8,425,474 B2
(45) Date of Patent: Apr. 23, 2013

(54) METHOD AND APPARATUS FOR DISPENSING A COMPOSITION

(75) Inventors: Bradley P. Glassman, Fairfield, NJ (US); Alan S. Goldstein, Fairfield, NJ (US); Daniel Glassman, Fairfield, NJ (US)

(73) Assignee: Fougera Pharmaceuticals Inc., Melville, NY (US)

( * ) Notice: Subject to any disclaimer, the term of this patent is extended or adjusted under 35 U.S.C. 154(b) by 444 days.

(21) Appl. No.: 12/187,781

(22) Filed: Aug. 7, 2008

(65) Prior Publication Data

US 2009/0048579 A1   Feb. 19, 2009

Related U.S. Application Data

(63) Continuation of application No. 11/649,794, filed on Jan. 5, 2007, now abandoned, which is a continuation of application No. 10/330,889, filed on Dec. 26, 2002, now abandoned.

(51) Int. Cl.
*A61M 31/00* (2006.01)
*A61J 1/06* (2006.01)
*B65D 35/28* (2006.01)

(52) U.S. Cl.
USPC .......... 604/275; 604/514; 206/528; 206/530; 222/92

(58) Field of Classification Search ........... 604/296, 604/241, 192, 212, 257, 285, 310; 222/92; 206/438, 570, 828
See application file for complete search history.

(56) References Cited

U.S. PATENT DOCUMENTS

| | | | |
|---|---|---|---|
| 184,776 A | 11/1876 | Grover |
| 208,761 A | 10/1878 | Post |
| 617,777 A | 1/1899 | Schweizer |
| 738,009 A | 9/1903 | Dews |
| 817,890 A | 4/1906 | Williams |
| 878,182 A | 2/1908 | Blake |

(Continued)

FOREIGN PATENT DOCUMENTS

| | | |
|---|---|---|
| DE | 2626830 A1 | 12/1977 |
| DE | 3324780 A1 | 1/1985 |

(Continued)

OTHER PUBLICATIONS

Definition of "tube", Merriam-Webster OnLine.*

(Continued)

*Primary Examiner* — Susan Su
(74) *Attorney, Agent, or Firm* — Choate, Hall & Stewart LLP; Charles E. Lyon; Danielle M. Nihan

(57) ABSTRACT

A pharmaceutical dispenser including a tube having an open end and a space filled with a composition, and an applicator including a first end removably coupled to the open end of the tube and a longitudinal portion with at least one aperture is described. The dispenser can also include a removable cover extending longitudinally and having a bore surrounding the longitudinal portion of the applicator. The composition may be an anal medication. A single dosage unit of the composition is usually contained in the tube, and the tube, applicator, and cover are disposable after use. Methods of using the dispenser include squeezing the tube, allowing the composition to exit the aperture of the applicator, and applying the composition to a target area.

7 Claims, 6 Drawing Sheets

U.S. PATENT DOCUMENTS

| | | | |
|---|---|---|---|
| 1,731,816 A | 10/1929 | Garhart | |
| 1,760,841 A | 5/1930 | Garhart | |
| 1,892,788 A | 1/1933 | Schwartz | |
| 1,909,209 A | 5/1933 | Miller | |
| 1,947,376 A | 2/1934 | Burrell | |
| 2,008,636 A | 7/1935 | Brynan | |
| 2,014,149 A | 9/1935 | Stafford | |
| 2,049,973 A | 8/1936 | Nesmith | |
| 2,197,579 A | 4/1940 | Hooper | |
| 2,249,832 A | 7/1941 | Hubschman | |
| 2,500,639 A | 3/1950 | Lermer | |
| 2,665,945 A | 1/1954 | Barton | |
| 2,677,373 A | 5/1954 | Barradas | |
| 2,683,456 A | 7/1954 | Pierson | |
| 2,734,665 A | 2/1956 | Flamm | |
| 2,873,886 A | 2/1959 | Miskel et al. | |
| 2,893,613 A | 7/1959 | Davis | |
| 2,896,237 A | 7/1959 | Owens et al. | |
| 2,952,861 A | 9/1960 | Reggio | |
| 2,974,666 A | 5/1961 | Coumbis et al. | |
| 3,016,173 A | 1/1962 | Stull | |
| 3,096,915 A | 7/1963 | Taylor | |
| 3,109,427 A | 11/1963 | Davidson | |
| 3,174,655 A | 3/1965 | Hurschman | |
| 3,225,763 A | 12/1965 | Waterman | |
| 3,275,000 A | 9/1966 | Bowen | |
| 3,361,304 A | 1/1968 | Thompson | |
| 3,486,503 A | 12/1969 | Merchlewitz et al. | |
| 3,777,949 A | 12/1973 | Chiquiari-Arias | |
| 3,912,082 A | 10/1975 | Gerner et al. | |
| 4,002,182 A | 1/1977 | Michel | |
| 4,011,879 A | 3/1977 | Roberts | |
| 4,159,718 A | 7/1979 | Bower | |
| 4,248,228 A | 2/1981 | Silver | |
| 4,421,504 A | 12/1983 | Kline | |
| 4,498,609 A | 2/1985 | Stock | |
| 4,514,384 A | 4/1985 | Gallina | |
| 4,560,376 A | 12/1985 | Cannon | |
| 4,752,288 A * | 6/1988 | Hussey | 604/111 |
| 4,773,551 A | 9/1988 | Rizzardi | |
| 4,808,166 A | 2/1989 | Davidov | |
| 4,972,969 A | 11/1990 | Randklev | |
| 5,042,690 A | 8/1991 | O'Meara | |
| 5,052,589 A | 10/1991 | O'Meara | |
| 5,056,689 A | 10/1991 | Heyl et al. | |
| 5,388,925 A | 2/1995 | Wilcox et al. | |
| 5,462,740 A | 10/1995 | Evenstad et al. | |
| 5,478,814 A | 12/1995 | Packman | |
| 5,501,370 A | 3/1996 | Okamura et al. | |
| 5,504,117 A | 4/1996 | Gorfine | |
| 5,531,703 A | 7/1996 | Skwarek et al. | |
| 5,588,559 A | 12/1996 | Vallet Mas et al. | |
| 5,588,560 A | 12/1996 | Benedict et al. | |
| 5,609,581 A | 3/1997 | Fletcher et al. | |
| 5,843,043 A | 12/1998 | Markus | |
| 5,885,597 A | 3/1999 | Botknecht et al. | |
| 6,117,877 A | 9/2000 | Fogel | |
| 6,136,337 A | 10/2000 | Kondo et al. | |
| 6,254,294 B1 | 7/2001 | Muhar | |
| 6,495,602 B1 * | 12/2002 | Bhagwat et al. | 514/588 |
| 6,706,728 B2 | 3/2004 | Hedenstrom et al. | |
| 7,997,460 B2 * | 8/2011 | Pardes et al. | 222/494 |
| 2004/0127861 A1 | 7/2004 | Glassman et al. | |
| 2007/0118083 A1 | 5/2007 | Glassman et al. | |

FOREIGN PATENT DOCUMENTS

| | | |
|---|---|---|
| DE | 3720346 A1 | 12/1988 |
| DE | 4107772 A1 | 9/1992 |
| FR | 2682873 A1 | 4/1993 |

OTHER PUBLICATIONS

Defintion of "elliptical cylinder", Wolfram Math World.*

Page from website http://www.preparationh.com, archived at http://web.archive.org, (Jun. 20, 2001).

English Translation of DT 2626830A1.

Product brochure for Colocort Hydrocortisone Rectal Suspension, USP by Paddock Laboratories, Inc., (Dec. 1999).

Berg, R. W, et al., "Etiologic factors in diaper dermatitis: the role of urine", *Pediatr Dermatol.*, 3(2), (Feb. 1986), 102-6.

Scheinfeld, N., "Diaper dermatitis: a review and brief survey of eruptions of the diaper area.", *Am J Clin Dermatol.*, 6(5), (2005), 273-81.

"Keratolytic—the Free Dictionary Definintion [online] Retrieved from the Internet at http://www.thefreedictionary.com/keralytic on Nov. 4, 2010", 2 pgs.

* cited by examiner

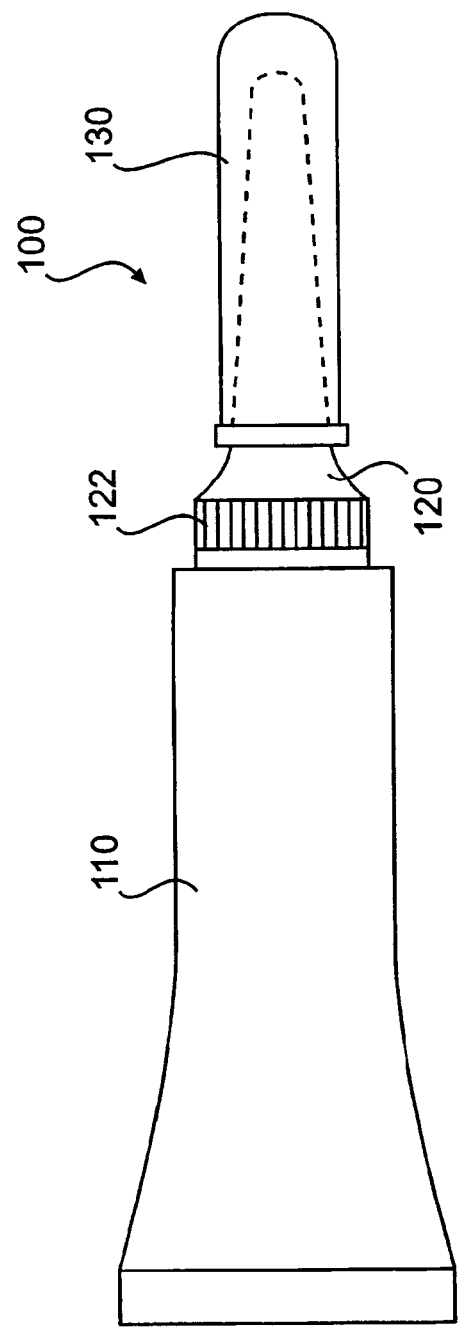
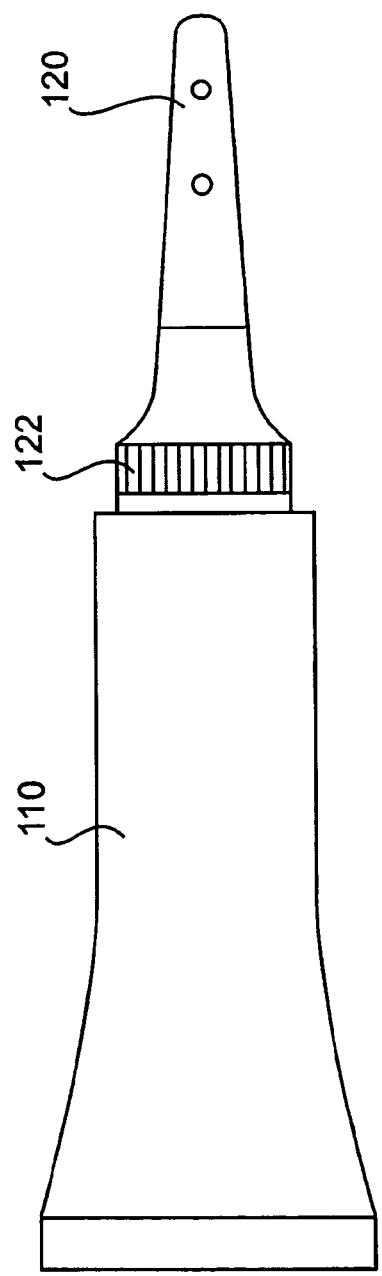

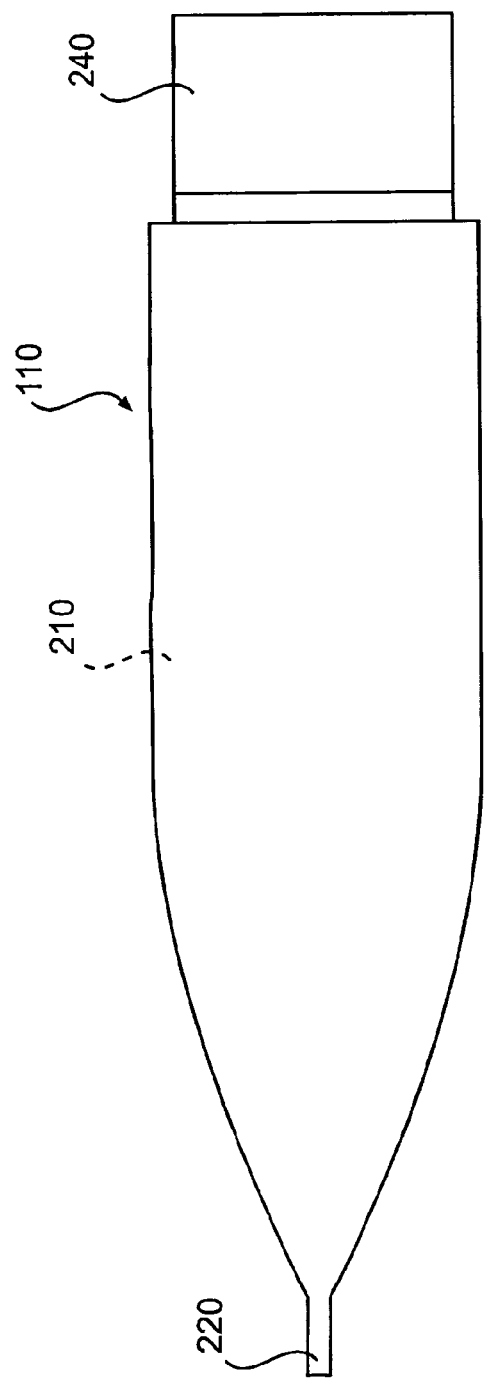
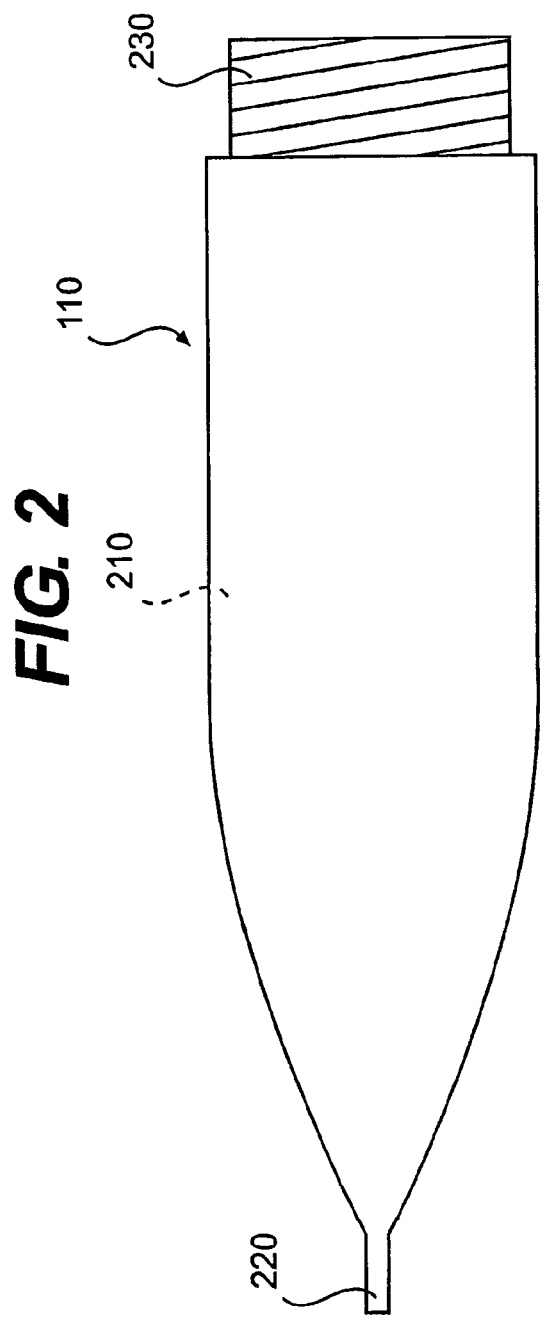
FIG. 2
FIG. 3

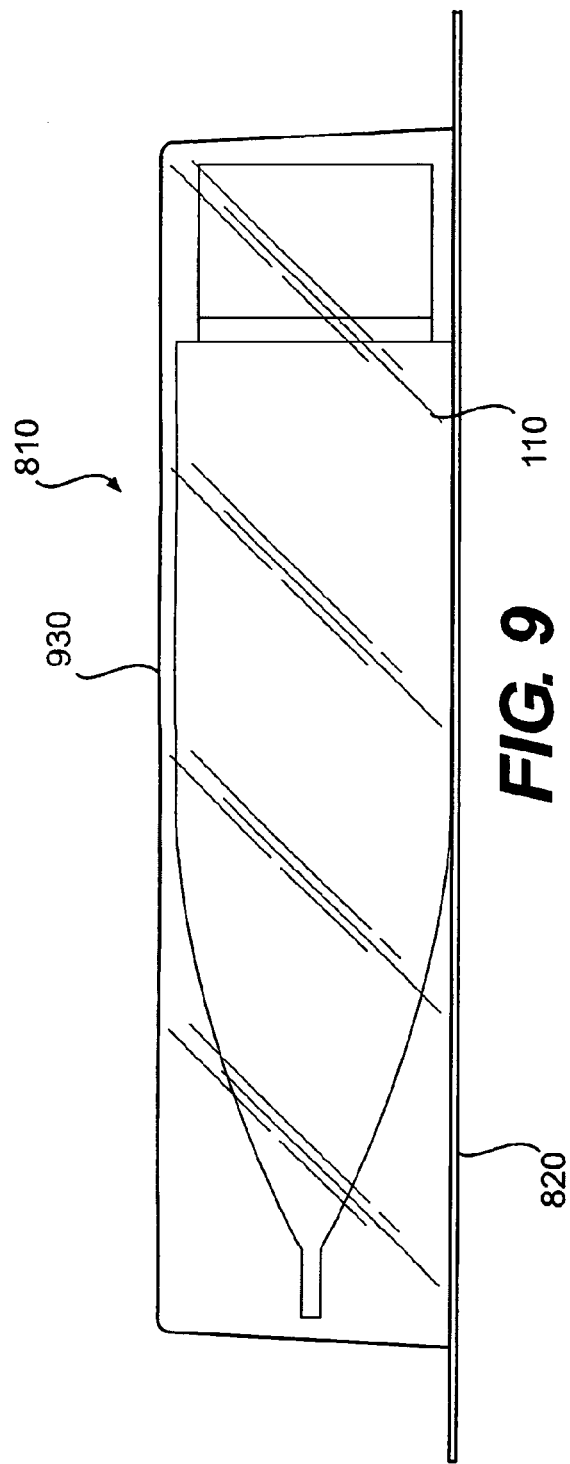
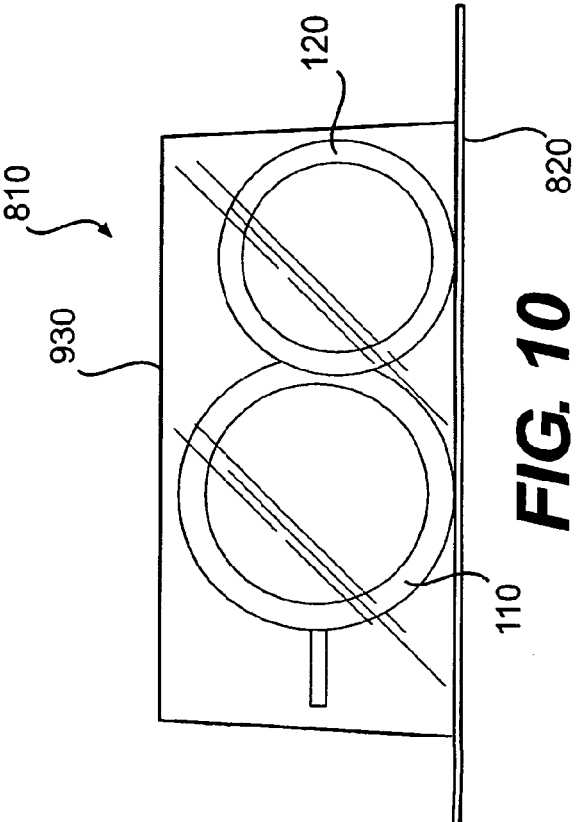

METHOD AND APPARATUS FOR DISPENSING A COMPOSITION

RELATED APPLICATIONS

This application is a Continuation of U.S. application Ser. No. 11/649,794, filed on Jan. 5, 2007 now abandoned, which is a Continuation of U.S. application Ser. No. 10/330,889, filed on Dec. 26, 2002 now abandoned. These applications are incorporated herein in their entirety.

TECHNICAL FIELD

The present invention relates to dispensers and, more particularly, to a container and applicator for dispensing a composition such as a pharmaceutical composition.

BACKGROUND

Containers used to hold compositions can perform various functions beyond that of simply housing the composition. For example, containers can be sized to dispense a specified dosage of the composition, as well as to assist in the application of the composition to a target area.

For example, in the context of medications used to treat anal ailments such as hemorrhoids, anal fissures, pruritis ani and similar conditions of the anal area (collectively, "hemorrhoids"), current packaging and application methods of compositions have generally been large, re-useable, bulky tubes accompanied by screw-on, multiple use applicators. See, for example, the applicator disclosed in U.S. Pat. No. 4,808,166 to Davidov. Treatments employing this historic methodology have generally resulted in unpleasant and inconvenient incidents for patients and potentially ineffective treatments. The unpleasant incidents include leaky and messy tubes containing the pharmaceutical compound and leaky and dirty applicators resulting from repeated use. Another inconvenience arises from the absolute necessity, for sanitary purposes, of thoroughly cleaning and drying a multiple use applicator after each treatment. Further, since the pharmaceutical is being dispensed from a large, multiple use tube, the potential for a patient to under or over-medicate his or herself exists because dosing amounts cannot be ascertained accurately.

It is therefore desirable to provide a dispenser and method for dispensing a composition that are sanitary, convenient to use, and provide accurate dosage amounts.

SUMMARY

The present invention relates to dispensers and, more particularly, to a container and applicator for dispensing a composition such as a pharmaceutical composition.

According to one aspect of the invention, a pharmaceutical dispenser includes a tube including an open end and defining a space filled with a composition, and an applicator including a first end removably coupled to the open end of the tube and longitudinal portion defining at least one aperture. The dispenser also includes a removable cover extending longitudinally and defining a bore surrounding the longitudinal portion of the applicator.

According to another aspect of the invention, a kit for application of anal medication includes a tube including an open end and defining a space filled with a composition; an applicator including a first end configured to mate with the open end of the tube and a longitudinal portion defining at least one aperture; and a sealed package defining an interior sized to accommodate the tube and the applicator.

According to yet another aspect of the invention, a method for dispensing a pharmaceutical includes: providing a tube including an open end and defining a space filled with a composition; removing a cap from the open end of the tube; mating a first end of an applicator with the open end of the tube; and dispensing the composition through an aperature defined by a longitudinal portion of the applicator onto a target area.

The above summary is not intended to describe each disclosed embodiment or every implementation of the present invention. The figures and the detailed description which follow more particularly exemplify these embodiments.

DESCRIPTION OF THE DRAWINGS

The invention may be more completely understood in consideration of the following detailed description of various embodiments of the invention in connection with the accompanying drawings, in which:

FIG. 1 is a top view of an example pharmaceutical dispenser made in accordance with the present invention;

FIG. 1A is a top view of the dispenser of FIG. 1 with the cover removed;

FIG. 2 is a side view of an example container including a cap made in accordance with the present invention;

FIG. 3 is a side view of the container of FIG. 2 with the cap removed;

FIG. 9 is a side view of the package of FIG. 8; and

FIG. 10 is an end view of the package of FIG. 8.

Figure 4:
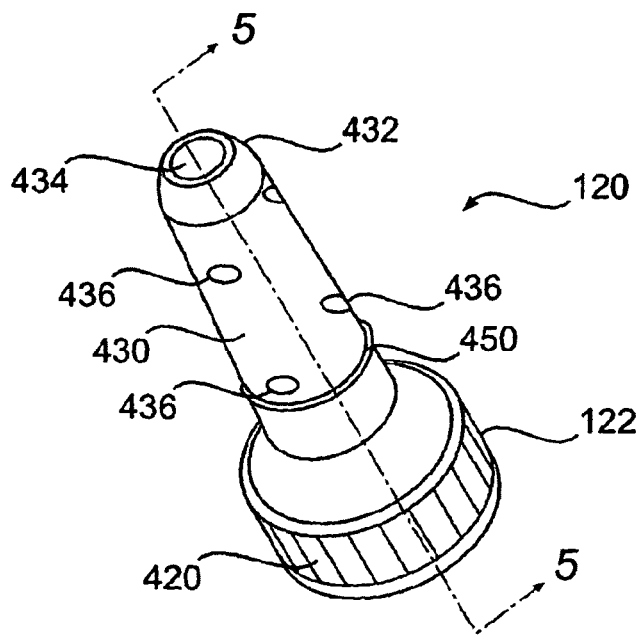
FIG. 4 is a perspective view of an example applicator made in accordance with the present invention.

While the disclosed subject matter is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present invention relates to dispensers and, more particularly, to a container and applicator for dispensing a composition such as a pharmaceutical composition.

Generally, the present invention is directed to a pharmaceutical dispenser including a container and an applicator. The container includes an interior for holding a composition, and an open end. The applicator includes a first end coupled to the open end of the container, and at least one aperture. The composition is dispensed out of the container, through the applicator, and out the aperture to a target area.

In the examples shown, the composition may be any composition used to treat anal ailments such as, for example, hemorrhoids, anal fissures, pruritis ani and similar conditions of the anal area (collectively, "hemorrhoids"). In the embodiment shown, the composition used is AnaMantle® HC available from Kenwood Therapeutics, a division of Bradley Pharmaceuticals, Inc. of Fairfield, N.J. AnaMantle® HC contains lidocaine HCl 3% and hydrocortisone acetate 0.5% microdispersed in an AcidMantle vehicle. Lidocaine is chemically designated as acetamide, 2-(diethylamino)-N-(2,6-dimethylphenyl). Hydrocortisone acetate has a chemical name pregn-4-ene-3, 20-dione, 21-(acetyloxy)-11, 17-dihydroxy-(11β)-. Other anal medications may also be selected as the composition, as desired. The example containers described herein hold a single dosage unit of the composition to be used for the relief of symptoms common to hemorrhoids, including swelling and inflammation of the anal area and rectal discomfort and itching.

Referring now to FIGS. 1 and 1A, an example pharmaceutical dispenser 100 is shown. The dispenser 100 includes a container, in the illustrated embodiment a tube 110, as well as an applicator 120 and a cover 130. A first end 122 of the applicator 120 is coupled to the tube 110, and the cover 130 is coupled to and surrounds a portion of the applicator 120.

Referring now to FIGS. 2 and 3, the example tube 110 is shown in more detail. The tube 110 includes an interior space 210 that is filled with the composition. A first end 220 of the tube 110 is sealed, while a second end 230 is open. The tube 110 is shown with a cap 240 screwed onto the open end 230 of the tube 110 in FIG. 2, and with the cap 240 removed in FIG. 3. With the cap 240 secured onto the open end 230 of the tube 110, the composition is maintained within the space 210 of the tube 110. When the cap 240 is removed, the tube 110 can be squeezed to dispense the composition out of the open end 230. In the example shown, the space 210 of the tube 110 is sized to hold a single dosage unit of the composition. Other dosage amounts may also be used. The example tube 110 is approximately 5.5-6.5 cm in length, although other dimensions for the tube may be used.

Figure 5:
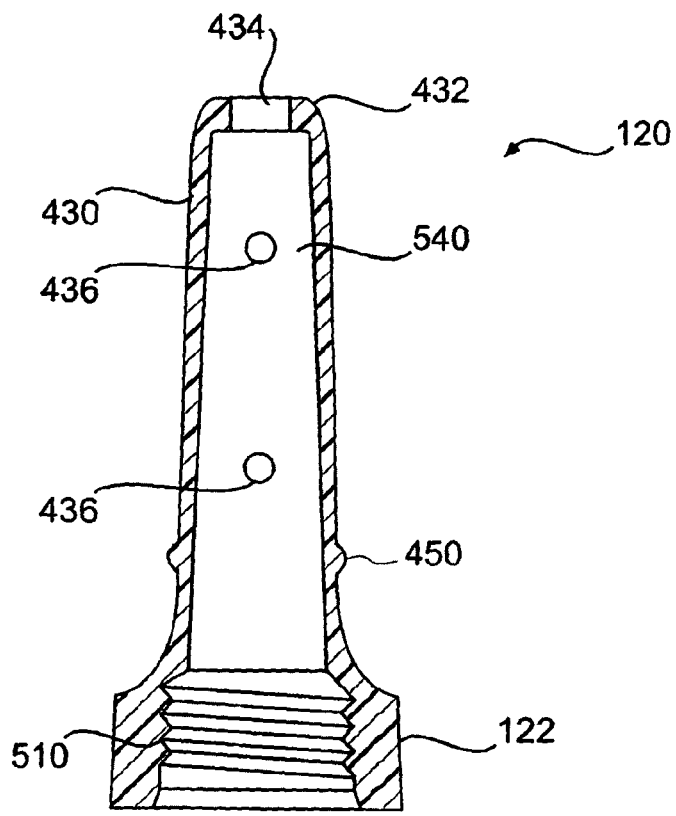
FIG. 5 is a cross-sectional view taken along line 5-5 of the applicator of FIG. 4.

Referring now to FIGS. 4 and 5, the example applicator 120 is shown in more detail. The first end 122 of the applicator 120 is open and includes a threaded bore 510 sized to screw onto the open end 230 of the tube 110 (see FIGS. 1 and 1A). An outer surface 420 of the first end 122 is ribbed to assist a user in screwing the applicator 120 onto the tube 110. The applicator 120 also includes a longitudinal portion 430 extending from the first end 122 to a second end 432. The longitudinal portion 430 is tapered as it extends from the first end 122 to the second end 432. An aperture 434 is defined at the second end 432. Further, additional apertures 436 may be positioned about the longitudinal portion 430. In the embodiment shown, the eight apertures 436 are positioned in a staggered-pair arrangement about the longitudinal portion 430. An internal cavity 540 formed within the applicator 120 (see FIG. 5) is fluidly coupled to the threaded bore 510, and the apertures 434 and 436 extend through the longitudinal portion 430 into the cavity 540. A circumferential rib 450 (see FIG. 4) is positioned about the outer circumference of the longitudinal portion 430 to hold the cover 130 in position on the applicator 120, as described further below. In the example shown, the applicator 120 is made of low density polyethylene and is approximately 4.5-5.0 cm in length. Other materials and lengths may also be used.

With the applicator 120 screwed onto the tube 110 and the cover 130 is removed (see FIG. 1A), the tube 110 can be squeezed, causing the composition to exit the open end 230 of the tube 110 and enter the bore 510. As the bore 510 is filled with the composition, the composition moves into the cavity 540 and is eventually forced out of the apertures 434 and 436 and onto a target area. As described further below, the applicator 120 is advantageously shaped for applying the pharmaceutical to the target area.

Figure 6:
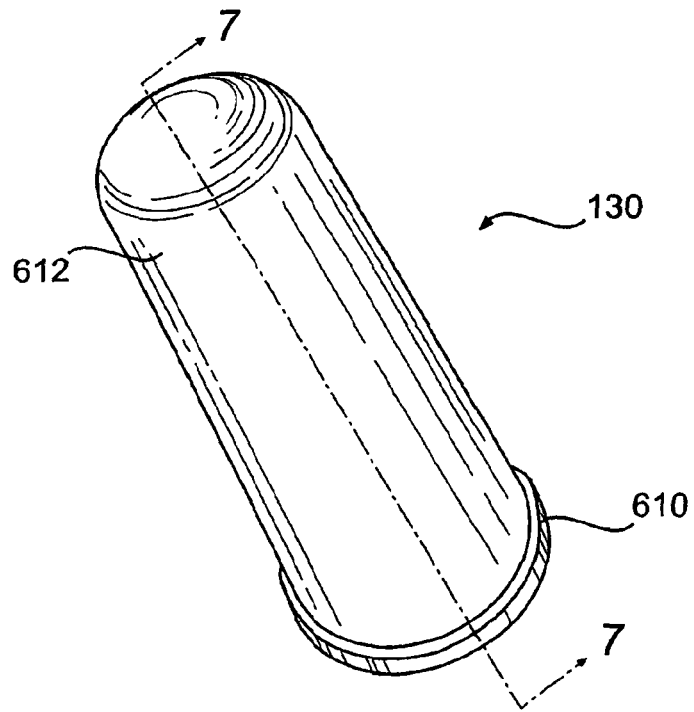
FIG. 6 is a perspective view of an example cover made in accordance with the present invention.
Figure 7:
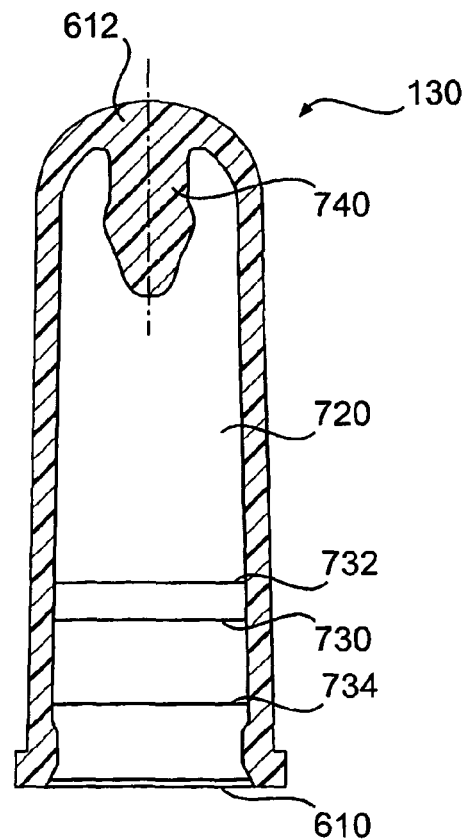
FIG. 7 is a cross-sectional view taken along line 7-7 of the cover of FIG. 6.

Referring now to FIGS. 6 and 7, the example cover 130 is shown in more detail. The cover 130 includes an open end 610 and cavity 720 sized to fit over and accept a portion of the longitudinal portion 430 of the applicator 120 (see FIG. 1). An opposite end 612 is closed. Circumferential ribs 730, 732, and 734 are formed on the interior surface of the cavity 720. The rib 734 is positioned to pass over the rib 450 of the applicator 120 as the cover 130 is slid over the applicator and thereby hold the cover 130 onto the applicator 120 by an interference fit. An optional protrusion 740 may extend from the end 612 to engage and partially extend through the aperture 434 formed in the second end 432 of the applicator 120 to further hold the cover 130 in place. In the example shown, the cover 130 is made of low density polyethylene and is approximately 3.5-4.0 cm in length. Other materials and lengths may also be used.

The cover 130 functions to protect and maintain the applicator 120 until use. In addition, the cover 130 (as well as the protrusion 740, if included) at least partially plugs the apertures 434 and 436 of the applicator 120 to reduce an amount of the composition that escapes the applicator 120 when the cover 130 is in place. In alternative embodiments, the cover 130 need not be used.

Figure 8:
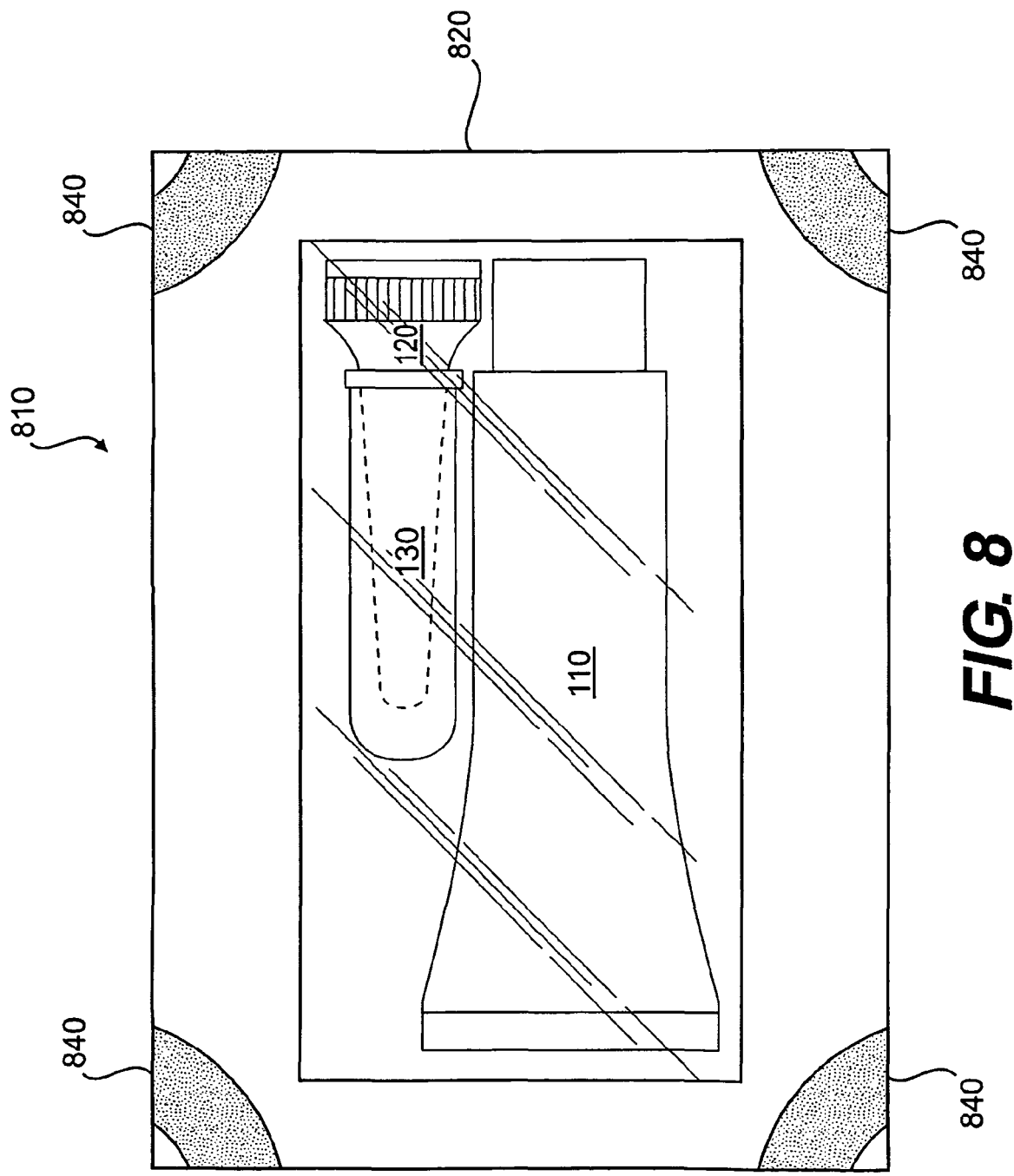
FIG. 8 is a top view of an example package enclosing a container, an applicator, and a cover in accordance with the present invention.

Referring now to FIGS. 8-10, an example package 810 is shown to hold the tube 110, applicator 120, and cover 130 for distribution. The package includes a base 820 (approximately 86.25 mm long and 61.00 mm wide in the embodiment shown) and an upper plastic bubble 930 surrounding the components of tile dispenser 100. In the example shown, the plastic bubble 930 rises approximately 17.50 mm above the base 820 and is made of 12-mil polyvinyl chloride plastic laminate. Also included in the example shown is a 1-mil child resistant aluminum foil that seals the package 810. The seal includes perforations 840 located at each corner of the base 820 to allow the seal to be peeled from the bubble 930 to provide access to the dispenser 100. The example package 810 can be obtained from Slispak, Inc. of Whippany, N.J., control number 2370. Another configuration for a package that may be used to house the dispenser is disclosed in U.S. Pat. No. 3,912,082 to Gerner et al., which is hereby incorporated by reference. Other configurations for packages used to hold the dispenser 100 may also be used.

An example method for using the dispenser 100 is a follows. First, the components of the dispenser 100 are removed from the package 810. Next, the cap 240 is removed from the tube 110, and the applicator 120 (with the cover 130 in place) is screwed firmly onto the open end 230 of the tube and tightened. While holding the tube 110, the cover 130 is then removed from the applicator 120, and the tube is squeezed to fill the applicator 120 until a small amount of the composition exits the apertures 434 and 436 formed in the applicator and lubricates the outer surface of the applicator 120 with the composition. Next, in the context of anal medication, the applicator is gently inserted into the anal area, and the tube 110 is squeezed as the applicator is moved around the target area. Once the application of the composition is completed, the dispenser 100, including the tube 110, the applicator 120, and the cover 130, is configured to be disposable.

There are many advantages to the dispenser 100 made in accordance with the present invention. For example, each tube can be a single-use tube that is filled with a precisely-measured single dosage unit of the composition to reduce errors associated with incorrect dosage applications. Further, because the dispenser 100 contains a single dosage unit and is disposable, it can be used for a prescribed treatment and thereafter discarded in its entirety by the user, thereby increasing sanitation. The tube is sealed, sanitary and has an easy-to-use screw-off top. The shape of the applicator, including the long, tapered longitudinal portion and smooth, closed sides allows for easy application of the composition. Further, because of the package and dispenser size, it is easily portable and can easily be carried in a user's pocket, small purse or small bag.

Although the composition has been described herein as an anal medication, it should be understood that other substances could also be used as the composition. For example, any other composition that is in a form such that it can be placed in the container and delivered by the applicator to a target area may also be used, such as other pharmaceutical agents, cosmetics, etc.

The present invention should not be considered limited to the particular examples described above, but rather should be understood to cover all aspects of the disclosed subject matter as fairly set out in the attached claims. For example, although the illustrated embodiments describe a threaded connection between the container and the applicator, other methods of connecting the two components, such as a snap-fit connection, may also be used. Various other modifications, equivalent processes, as well as numerous structures to which the present invention may be applicable will be readily apparent to those of skill in the art to which the present invention is directed upon review of the instant specification.

What is claimed is:

1. A pharmaceutical dispenser comprising:
   a tube including a threaded open end and defining a space filled with a single dosage unit of a composition that consists of lidocaine and hydrocortisone acetate in a vehicle;
   a threaded cap configured to be screwed onto the open end of the tube;
   an applicator including a first end removably coupled to the open end of the tube and a longitudinal portion defining a plurality of apertures, wherein one of the plurality of apertures is located at a second end of the longitudinal portion and the applicator is configured to be removable from the tube;
   a removable cover extending longitudinally and defining a bore surrounding the longitudinal portion of the applicator;
   wherein the tube is configured to be squeezable so that the composition is dispensed through the plurality of apertures when the tube is squeezed.

2. The dispenser of claim 1, wherein the tube and applicator are disposable after use.

3. A kit for application of anal medication, the kit comprising:
   a tube including a threaded open end and defining a space filled with a single dosage unit of a composition that consists of lidocaine and hydrocortisone acetate in a vehicle;
   a threaded cap configured to be screwed onto the open end of the tube;
   an applicator including a first end configured to mate with the open end of the tube and a longitudinal portion defining a plurality of apertures, wherein one of the plurality of apertures is located at a second end of the longitudinal portion and the applicator is configured to be removable from the tube;
   wherein the tube is configured to be squeezable so that the composition is dispensed through the plurality of apertures when the tube is squeezed; and
   a sealed package defining an interior sized to accommodate the tube, the cap and the applicator.

4. The kit of claim 3, wherein the package is a blister pack.

5. The kit of claim 4, wherein the blister pack is a child resistant seal.

6. The kit of claim 3, wherein the package, tube, and applicator are disposable after use.

7. A method for dispensing a pharmaceutical, comprising:
   providing a tube including a threaded open end and defining a space filled with a composition that consist of lidocaine and hydrocortisone acetate in a vehicle;
   removing a threaded cap from the open end of the tube;
   mating a first end of an applicator with the threaded open end of the tube, wherein the applicator includes a first end configured to mate with the open end of the tube and a longitudinal portion defining a plurality of apertures, wherein one of the plurality of apertures is located at a second end of the longitudinal portion; and
   dispensing the composition through the plurality of apertures in the longitudinal portion of the applicator onto a target area.

* * * * *